United States Patent
Kane et al.

[19]

[11] Patent Number: 6,030,783
[45] Date of Patent: Feb. 29, 2000

[54] PHOTO-POTENTIATION OF CISPLATIN CHEMOTHERAPY

[75] Inventors: Stefanie A. Kane, Schwenksville, Pa.; Stephen J. Lippard, Cambridge, Mass.

[73] Assignee: Massachusetts Institute of Technology, Cambridge, Mass.

[21] Appl. No.: 09/015,003

[22] Filed: Jan. 28, 1998

Related U.S. Application Data

[60] Provisional application No. 60/037,244, Jan. 31, 1997.

[51] Int. Cl.[7] .............................. C12Q 1/68; C12N 13/00; A01N 59/16; A61K 33/24
[52] U.S. Cl. .............................. 435/6; 435/7.1; 435/7.23; 435/173.1; 424/617; 424/649
[58] Field of Search ................................ 435/6, 7.1, 7.23, 435/173.1; 424/617, 649

[56] References Cited

U.S. PATENT DOCUMENTS

| | | | |
|---|---|---|---|
| 5,359,047 | 10/1994 | Donahue et al. | 536/23.5 |
| 5,670,621 | 9/1997 | Donahue et al. | 530/350 |
| 5,705,334 | 1/1998 | Lippard et al. | 435/6 |
| 5,879,917 | 3/1999 | Essigmann et al. | 435/172.1 |

OTHER PUBLICATIONS

"Photoreactivity of Platinum(II) in Cisplatin–Modified DNA Affords Specific Cross–Links to HMG Domain Proteins," Kane et al., *Biochemistry*, 1996, 35, 2180–2188.

"UVA–Photosensitivity of cis–Diamminedichloro–Platinum(II)–Modified DNA," Payet et al., *Metal–Based Drugs*, 1995, 2, 137–161.

*Primary Examiner*—Kenneth R. Horlick
*Attorney, Agent, or Firm*—Testa, Hurwitz & Thibeault, LLP

[57] ABSTRACT

Methods disclosed herein capitalize on the discovery that DNA Structure Specific Recognition Proteins (SSRPs) can be induced to bind covalently to genomic lesions formed by chemotherapeutic agents, particularly cisplatin-type agents, by photo-irradiation with ultraviolet light. Methods and compositions based on this discovery are provided for sensitizing particular eukaryotic cells to killing by chemotherapeutic agents, particularly cisplatin-type drugs. Methods and compositions also are provided for potentiating cytotoxicity of a chemotherapeutic agent, particularly a cisplatin-type agent.

42 Claims, 3 Drawing Sheets

INTRASTRAND CROSS-LINK        PROTEIN-DNA CROSS-LINK

PHOTO-POTENTIATION OF CISPLATIN CHEMOTHERAPY

REFERENCE TO RELATED APPLICATIONS

This application claims priority under 35 U.S.C. §119(e) to commonly-owned and copending Provisional Application Ser. No. 60/037,244, filed Jan. 31, 1997.

GOVERNMENT SUPPORT

Work described herein was supported by grants from the National Cancer Institute, and the National Institutes of Health. The United States Government has certain rights in the invention.

FIELD OF THE INVENTION

The present invention relates generally to novel chemotherapeutic methods for cancer management.

BACKGROUND OF THE INVENTION

Cancer chemotherapy is based on the use of drugs that are selectively toxic (cytotoxic) to cancer cells (also referred to herein as tumorigenic cells, transformed cells or neoplastic cells). Harrison's Principles of Internal Medicine, Part 11 Hematology and Oncology, Ch. 296, 297 and 300–308 (12th ed. 1991). A preferred class of chemotherapeutic drugs inflict damage on cellular DNA. Drugs of these classes generally are referred to as genotoxic. Two widely used genotoxic anticancer drugs are cisplatin [cis-diamminedichloroplatinum(II)] and carboplatin [diaminine (1,1-cyclobutane dicarboxylato)platinum(II)]. Bruhn et al. (1990), 38 Prog. Inorg. Chem. 477, Burnouf et al. (1987), 84 Proc. Natl. Acad. Sci. USA 3758, Sorenson and Eastman (1987), 48 Cancer Res. 4484 and 6703, Pinto and Lippard (1985), 82 Proc. Natl. Acad. Sci., USA 4616, Lim and Martini (1984), 38 J. Inorg. Nucl. Chem. 119, Lee and Martin (1976), 17 Inorg. Chim. Acta 105, Harder and Rosenberg (1970), 6 Int. J. Cancer 207, Howle and Gale (1970), 19 Biochem. Pharmacol 2757. Cisplatin and/or carboplatin currently are used in the treatment of selected, diverse neoplasms of epithelial and mesenchymal origin, including carcinomas and sarcomas of the respiratory, gastrointestinal and reproductive tracts, of the central nervous system, and of squamous origin in the head and neck. Harrison's Principles of Internal Medicine (12th ed. 1991) at Ch. 301. Cisplatin currently is preferred for the management of testicular carcinoma, and in many instances produces a lasting remission. Loehrer and Einhorn (1984), 100 Ann. Int. Med. 704. Susceptibility of an individual neoplasm to a desired chemotherapeutic drug or combination thereof often, however, can be accurately assessed only after a trial period of treatment. The time invested in an unsuccessful trial period poses a significant risk in the clinical management of aggressive malignancies.

U.S. Pat. No. 5,359,047 (the teachings of which are incorporated herein by reference) recounts the discovery that eukaryotic cells contain one or more intracellular structure specific recognition proteins, or SSRPs, that bind to 1,2-dinucleotide intrastrand adducts formed in cellular DNA by therapeutically useful genotoxic metal coordination compounds, such as platinum(II) and platinum(IV) compounds. The class of genotoxic noble metal coordination compounds that form SSRP-recognized genomic lesions includes cisplatin (cis-diamminedichloroplatinum(II) or cis-DDP), carboplatin (diammine(1,1-cyclobutane-dicarboxylato)platinum(II), cis-diamminetetrachloroplatinum(IV), iproplatin (CHIP), DACCP, malonatoplatin, cis-dichloro(ethylenediamine) platinum(II), cis-dichloro(1,2-diaminocyclohexyl)platinum (II), and the like. For convenience, SSRP recognized 1,2-intrastrand dinucleotide adducts formed by any member of this class are referred to herein as cisplatin-type lesions (or adducts). Such lesions are formed by substitution of the cis-configured labile moieties of the genotoxin by atoms of the nucleotide bases, usually adenosine (A) or guanosine (G) residues. This produces a crosslink, bridged by the noble metal atom (e.g., platinum) between two vicinal, adjacent or paired nucleotide bases. Platinum-bridged crosslinks between adjacent adenosine and guanosine residues within a single polynucleotide strand (1,2-intrastrand dinucleotide adducts or lesions) of double stranded DNA are abbreviated herein as 1,2-d(A^G) and 1,2-d(G^G) lesions. The structural distortion associated with cisplatin-type genomic lesions produces a characteristic three-dimensional DNA structural motif, comprising a bend in the direction of the major groove.

The rate of cellular repair of genotoxin-induced DNA damage, as well as the rate of cell growth via the cell division cycle, affects the effectiveness of genotoxin therapy. Unrepaired lesions in a cell's genome can impede DNA replication, impair the replication fidelity of newly synthesized DNA or hinder the expression of genes needed for cell survival. Thus, one determinant of a genotoxic agent's cytotoxicity (propensity for contributing to cell death) is the resistance of genomic lesions formed therefrom to cellular repair. Genotoxic agents that form persistent genomic lesions, e.g., lesions that remain in the genome at least until the cell commits to the cell cycle, generally are more effective cytotoxins than agents that form transient, easily repaired genomic lesions. Hence, genotoxic agents that form persistent genomic lesions are preferred for use as chemotherapeutic agents in the clinical management of cancer.

When SSRP binds to a cisplatin-type genomic lesion, a DNA:protein complex is formed, such that the sterically large SSRP becomes localized in the immediate vicinity of the genomic lesion. This complex can be detected visually using techniques described in U.S. Pat. No. 5,359,047, including modified Western (Southwestern) blotting and electrophoretic mobility shift analysis (EMSA, also known as bandshift analysis). The SSRP is large enough to sterically obscure (cover) a region of cellular DNA extending from the lesion site in both the 5' and 3' direction for at least about five base pairs, and to shield the genomic lesion from repair by the cell's enzymatic DNA repair machinery. SSRP-shielded lesions persist in the genome longer than unshielded lesions. SSRP-shielded lesions accordingly are more effective for prejudicing the fidelity of DNA replication, hindering the expression of genes relevant to cell survival, and otherwise contributing to disarray of the cell's nuclear architecture. One or more of the foregoing can contribute to cell death, e.g., by triggering apoptosis. Indeed, there have been several reports in the literature that actively dividing cells that are unable to carry out DNA repair are extremely sensitive to cisplatin. Fraval et al. (1978), 51 *Mutat. Res.* 121, Beck and Brubaker (1973), 116 *J. Bateriol* 1247.

Most SSRPs reported thus far comprise at least one high mobility group, or HMG, structural domain. As described in U.S. Pat. No. 5,359,047, the HMG domain is involved in recognition of, and complex formation with, cisplatin-type DNA lesions. Thus, it is believed that all known and currently unknown cellular HMG domain proteins have SSRP activity for cisplatin-type lesions. Certain HMG domain proteins useful as SSRPs have been characterized in the literature as transcription factors that control or modulate the expression of one or more cellular genes, including genes that are relevant to cell metabolism or cell secretory function. Binding of such transcription factors to cisplatin-type lesions enhances cisplatin cytotoxicity, by disrupting cell metabolism and/or vital functions.

However, the DNA:protein complex formed by SSRP binding at the lesion site is non-covalent in nature. Thus, the SSRP-mediated repair shielding effect is dependent on non-covalent binding and is subject to dissociation of the DNA:protein complex.

Needs remain for increasing the incidence of selective cell death by increasing persistence of genomic lesions in tumorigenic cells. Needs remain also for enhancing effectiveness of chemotherapeutic drugs, such that satisfactory cell killing can be achieved with lower doses than are currently needed. Poignant needs remain for chemotherapeutic drugs with improved selectivity for destroying tumorigenic cells. Particularly poignant needs remain for ways to render tumorigenic cells selectively more vulnerable to killing through chemotherapy.

SUMMARY OF THE INVENTION

This invention rests on the discovery that photo-irradiation of DNA bearing cisplatin-type genotoxin lesions generates specific covalent cross-links between the DNA and SSRP HMG domains. As a result, SSRPs become tethered to the genomic lesion sites via a covalent bond to the genotoxin, which, in turn, is bound covalently to a suitable nucleotide base at the lesion site. Thus, cisplatin acts as a covalent bridge between the DNA and the SSRP. The presence of this covalent crosslink improves stability and persistence of SSRP-shielded genomic lesions. It therefore is a general object of this invention to provide improved methods for enhancing persistence of DNA lesions in the genome of eukaryotic cells, especially tumorigenic cells.

The objects of this invention more specifically include providing improved methods for enhancing cytotoxicity of cisplatin-type therapeutic agents; for enhancing selective cytotoxicity of such agents in tumorigenic cells, and, for rendering tumorigenic cells selectively vulnerable to cisplatin-type chemotherapy.

A first aspect of the invention provides a method for potentiating cytotoxicity of a chemotherapeutic agent that inflicts genomic lesions on cellular DNA by contacting a eukaryotic cell with the chemotherapeutic agent, so that the agent produces a genomic lesion in the DNA of the cell; incubating the cell in the presence of the agent for a time sufficient for one or more SSRPs present in the cell to bind to the genomic lesion produced by the agent and form a non-covalent DNA:protein complex; and photo-irradiating the complex so that a covalent bond is formed between the SSRP and the genomic lesion. A second aspect of the invention provides a platinum-bridged covalent DNA:protein complex produced as a result of practicing the methods disclosed herein. The complex comprises an SSRP bound via a covalent crosslink to the genomic lesion inflicted by a chemotherapeutic agent. The DNA:protein complex is refractory to repair by excinuclease and other DNA repair enzymes.

In a preferred embodiment, the invention provides a method for potentiating cytotoxicity of a platinum coordination compound that inflicts genomic lesions on mammalian cellular DNA (the genomic lesions comprising 1,2-intrastrand dinucleotide adducts of the platinum coordination compound) by contacting a mammalian cell, for example a tumorigenic cell, with the platinum coordination compound so that a genomic lesion is produced in the cell's DNA; incubating the cell in the presence of the compound for a time sufficient for an SSRP comprising at least one HMG domain to bind to the genomic lesion, forming a non-covalent DNA:protein complex; and photo-irradiating the complex so that a covalent bond is formed therein, tethering the protein to the genomic lesion.

In another preferred embodiment, invention provides a method for potentiating cytotoxicity of a platinum coordination compound selected from cisplatin, iproplatin and carboplatin by contacting a tumorigenic mammalian cell with the platinum coordination compound so that a platinated genomic lesion is produced in the DNA of the tumorigenic cell; incubating the tumorigenic cell in the presence of the compound for a time sufficient for an HMG domain SSRP protein to bind to the genomic lesion, forming a non-covalent DNA:protein complex; and photo-irradiating the complex with ultraviolet light having a wavelength of about 300 nm, so that a covalent bond is formed in the complex, tethering the HMG domain SSRP protein to the genomic lesion.

In still other preferred embodiments, the invention provides DNA:protein complexes comprising an SSRP bound via a covalent crosslink to a genomic lesion in DNA produced by a chemotherapeutic agent. Similarly, the invention provides compositions comprising an SSRP tethered covalently to double-stranded DNA via covalent bonds to a platinum compound linking the SSRP to the DNA. In a preferred embodiment, the SSRP comprises at least one HMG domain. These covalent DNA:protein complexes may be produced according to the methods described herein.

Advantageously, then, the invention provides for the formation of persistent and therefore cytotoxic lesions, and is expected to allow the use of low doses of cisplatin-type genotoxins, formerly considered poorly effective or ineffective for cell killing. The invention also may enhance the effectiveness of additional genotoxins, including genotoxins formerly considered poorly effective or ineffective as cytotoxins. Further, the invention may reconstitute the cytotoxic susceptibility of cells that are refractory to killing by genotoxins, including cells that express a gene for multiple drug resistance.

These and other objects, along with advantages and features of the invention disclosed herein, will be apparent from the description, drawings and claims that follow.

BRIEF DESCRIPTION OF THE DRAWINGS

The foregoing and other objects, features and advantages of the present invention, as well as the invention itself, will be more fully understood from the following description of preferred embodiments, when read together with the accompanying drawings, in which.

DETAILED DESCRIPTION OF PREFERRED EMBODIMENTS

Figure 1:
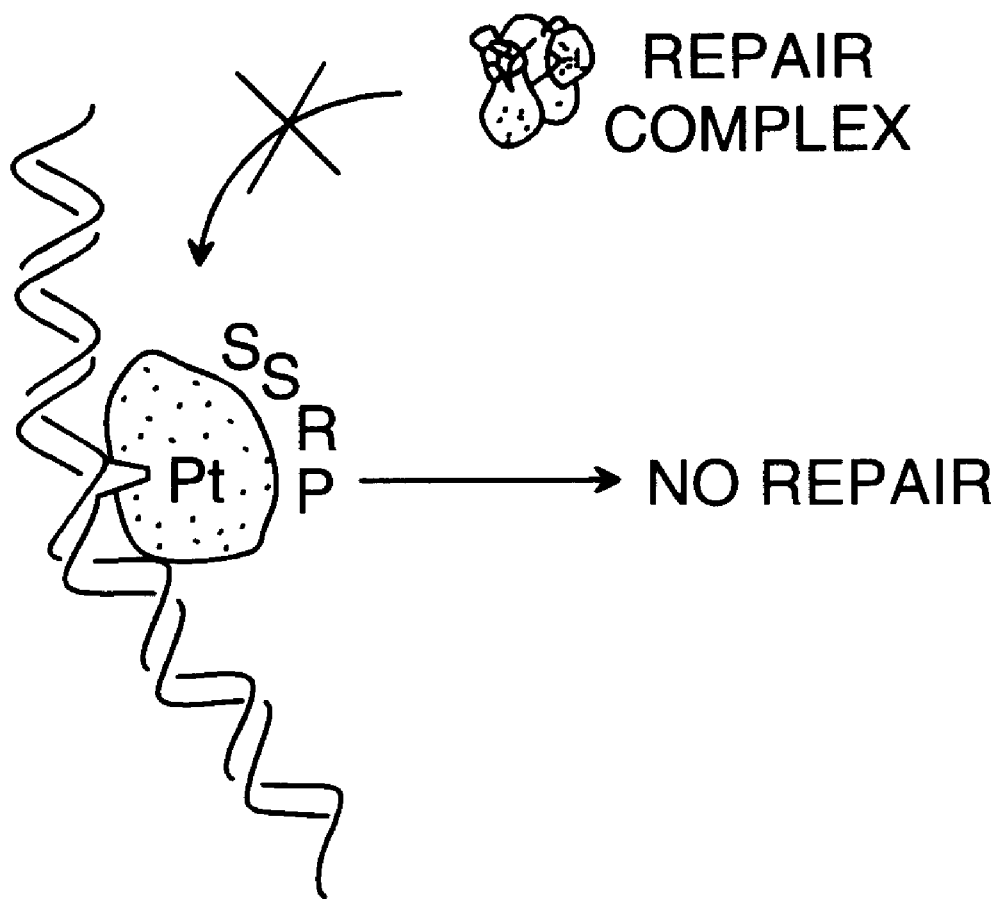
FIG. 1 is a schematic representation of the steric shielding by SSRP of a cisplatin-type genomic lesion from repair by the cellular enzymatic DNA repair machinery.

Broadly, the invention capitalizes still further on the principle disclosed in U.S. Ser. No. 08/328,809, filed Oct. 25, 1994, U.S. Pat. No. 5,705, 334, the teachings of which are incorporated herein by reference, that DNA structure specific recognition proteins (SSRPs) contribute to the cytotoxic efficacy of chemotherapeutic genotoxins by binding to toxin-associated genomic lesions and sterically shielding the lesions from repair. That is, lesion-bound SSRP hinders access to the lesion site by elements of the cell's enzymatic DNA repair machinery, including the multisubunit enzyme, excinuclease. This principle is illustrated schematically in FIG. 1. SSRP-shielded lesions persist in the genome and are more likely than unshielded lesions to contribute to the disarray of cellular metabolism and thus cell death. It is thought that SSRP recognized genomic lesions, although produced by the binding of genotoxic agents to cellular DNA, resemble naturally occurring structural motifs in the genome. Such naturally occurring motifs may be associated with the packaging of cellular DNA in chromatin, or the participation of chromatin in higher ordered aspects of nuclear architecture. Alternatively, such naturally occurring motifs may be associated with DNA replication, gene transcription, transcriptional repression, and like processes involving gene expression.

Chemotherapeutic agents useful in the present invention effectively form genomic lesions or adducts in cellular DNA. Metal coordination compounds are effective chemotherapeutic agents in this regard, especially platinum compounds. The class of genotoxic noble metal coordination compounds that form SSRP-recognized genomic lesions includes cisplatin (cis-diamminedichloroplatinum(II) or cis-DDP), carboplatin (diammine(1,1-cyclobutane-dicarboxylato)platinum(II), cis-diamminetetrachloro platinum(IV), iproplatin (CHIP), DACCP, malonatoplatin, cis-dichloro(ethylenediamine) platinum(II), cis-dichloro(1, 2-diaminocyclohexyl)platinum(II), and the like. Preferably, these platinum compounds are platinum(II) or platinum(IV) compounds having a platinum atom linked covalently to a pair of cis configured substitutionally labile moieties and a pair of cis configured electron donor moieties. All such compounds are defined as cisplatin-type compounds or drugs. Preferred examples of these compounds include cisplatin, carboplatin and ibroplatin.

The adduct or lesion formed most frequently by the binding of cisplatin drugs to cellular DNA is the 1,2-intrastrand dinucleotide adduct, in which adjacent nucleotide bases become crosslinked directly through a platinum bridge. 1,2-d(A^G) and 1,2-d(G^G) adducts account together for approximately 90% of the DNA lesions produced in vivo by cisplatin and cisplatin-type drugs. The 1,2-intrastrand cisplatin-type adduct structurally comprises an unwinding element of about 13° at the site of a fairly inflexible bend in the double helix of 32–34° toward the major groove. Bellon and Lippard (1990), 35 *Biophys. Chem.* 179, Rice et al. (1988), 85 *Proc. Natl. Acad. Sci. U.S.A.* 4158. The platinum bridge itself, together with substituents of the platinum atom located trans to the substitutionally labile moieties, projects into the major groove.

Eukaryotic proteins comprising one or more HMG domains (Grosschedl et al. (1994), 10 *Trends Genet.* 94; Jantzen et al. (1990), 344 *Nature* 830) bind specifically to 1,2-intrastrand d(G^G) and d(A^G) cisplatin-type DNA adducts, but not to other types of lesions in DNA, even when produced by cisplatin. Bruhn et al. (1992), 89 *Proc. Natl. Acad. Sci USA* 2307; Pil and Lippard (1992), 256 *Science* 234. U.S. Ser. No. 08/258,442, U.S. Pat. No. 5,670,621, and U.S. Pat. No. 5,359,047 describe the use of probe DNA bearing cisplatin-type lesions to identify structure specific recognition proteins in eukaryotic cells. A cellular SSRP present in mammalian (human (HeLa) and hamster (V79)) cell extracts bound specifically to double stranded probe DNA bearing lesions produced by cisplatin, cis-dichloro (ethylenediamine)platinum(II) and cis-dichloro(1,2-diaminocyclohexane) platinum(II). All such SSRP proteins bind non-covalently to the solvent exposed, partially unwound minor groove side of the lesion.

It now has been discovered that photo-irradiation of DNA bearing lesions inflicted by cisplatin-type drugs generates specific covalent cross-links between lesioned DNA and SSRP HMG domains. The photoreactivity of square-planar platinum(II) complexes is well documented. For example, irradiation of cis-[Ptpy$_2$Cl$_2$] (i.e., bis (pyridine) dichloro platinum (II)) with 313 nm light results in two simultaneous reactions, photoisomerization and photodissociation of a pyridine ligand. Moggi et al. (1971) 3 *Mol. Photochem.* 141. Loss of pyridine produces a tetracoordinated solvento complex which can recombine with ligand to give a mixture of cis- and trans-[Ptpy$_2$Cl$_{21}$]. By contrast, trans-[Ptpy$_2$Cl$_2$] is insensitive to irradiation at the same wavelength. Cis-trans photoisomerization also occurs in cis-[Pt(glycinato)$_2$] (i.e., bis (glycinato) platinum (II)) upon excitation of the ligand-field band at 313 nm. Balzani & Carassiti (1968) 72 *J. Phys. Chem.* 383. The products of photochemical reactions of carboplatin have also been characterized. Liu et al. (1994) Ser. B 37 *Sci China* 799. Excitation of the ligand-field band (313 nm) leads to photosubititution, producing diaquadiammineplatinum(II) and tetraaquaplatinumr(II). By contrast, excitation of the charge-transfer band (254 nm) results in redox chemistry. Cisplatin itself undergoes photosubstitution reactions, losing an amine ligand when irradiated with 300–350 nm light. Macka et al. (1994) 83 *J. Pharm. Sci.* 815.

While not wishing to be bound to any specific mechanism or means of operation underlying the present invention, it is believed that the mechanism of protein photo-cross-linking by cisplatin-modified DNA involves photosubstitution of one of the ligands by a protein residue, Lys-6 in the case of HMG domain B (see below). Furthermore, the observed cross-links seem to result from labilization of a platinum-purine bond. Support for this proposal comes from two separate studies. In gel mobility shift assays, HMG1 did not bind to a platinated DNA probe that had been preirradiated, suggesting that the bent DNA structure was no longer intact. Photodissociation of a guanine ligand would result in a platinum that was no longer bound bivalently to DNA and hence unable to be recognized by HMG domains. Secondly, the chemical reactivity of the guanine bases coordinated to platinum in the 15Pt-HMG domain B photo-cross-linked complex was studied by using Maxam-Gilbert sequencing chemistry (See Example 5 below). Platinated guanine bases do not react with the guanine- or purine-specific reagents, dimethyl sulfate or formic acid, respectively, because their N-7 atoms are coordinated to the metal ion. Comess et al. (1990) 29 *Biochemistry* 2102; Brabec & Leng (1993) 90 *Proc. Natl. Acad Sci. USA* 5345. The following species were subjected to this type of sequencing analysis: the oligonucleotide 15Pt that had been complexed in a non-covalent manner with HMG domain B; the fill-length photo-cross-linked 15Pt-HMG domain B complex; and products resulting from routine endoproteinase Asp-N digestion of the cross-linked 15Pt-HMG domain B complex. The guanine bases in the unirradiated oligonucleotide, as well as in the oligonucleotide that had undergone non-covalent complexation with HMG domain B, did not react with these reagents, as expected. In the cross-linked protein-DNA complex and in the proteolyzed peptide-DNA complex, the guanines were reactive, indicating loss of platinum from these sites.

Figure 2A:
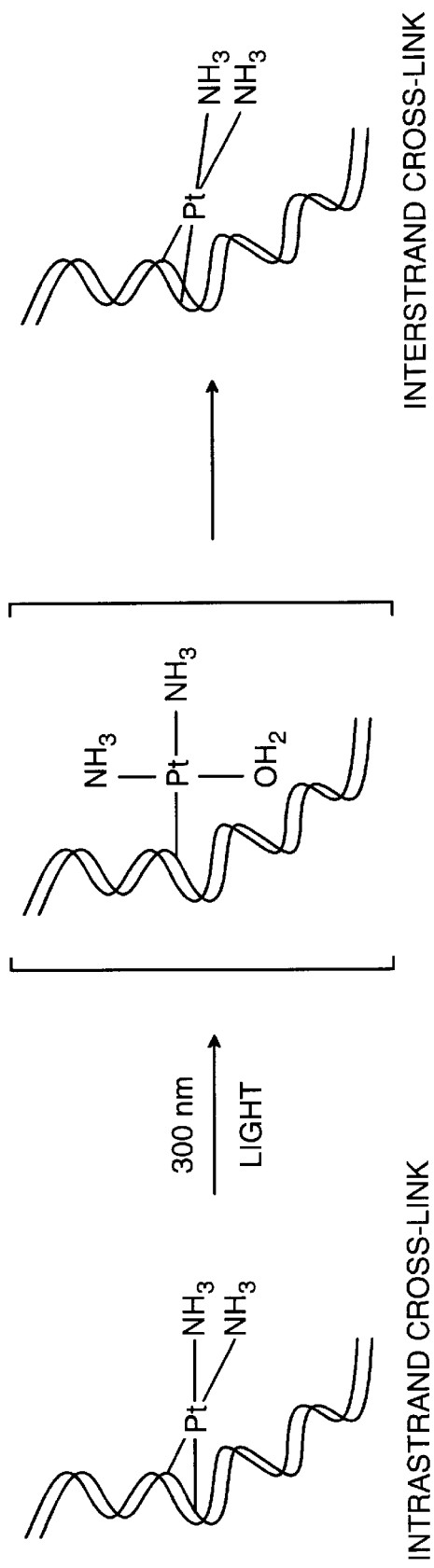
FIG. 2A is a schematic representation showing the mechanism of photoinduced DNA interstrand cross-linking by cisplatin.
Figure 2B:
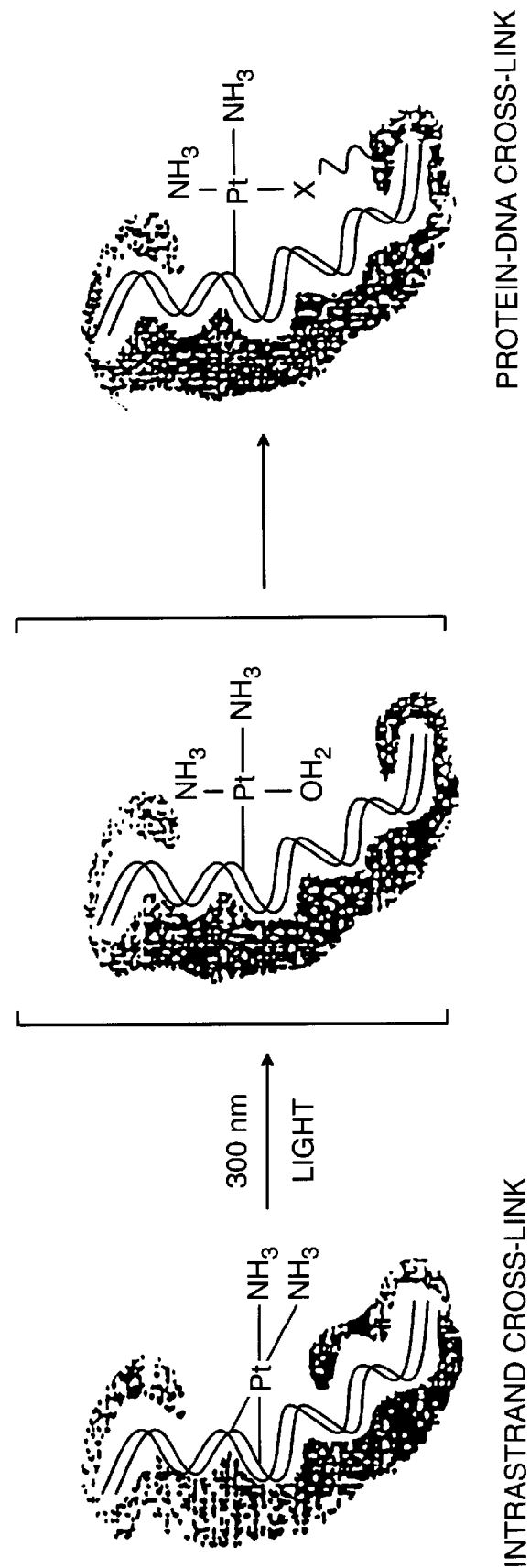
FIG. 2B is a schematic representation showing the mechanism of photoinduced DNA and protein cross-linking by cisplatin-modified DNA.

In other words, irradiation with UV light results in photodissociation of an involved purine ligand, producing a reactive intermediate in which the vacant site is filled with a more labile ligand, presumably a water molecule. This labile ligand is then displaced by a nucleophile, such as a nucleobase on the opposing DNA strand, producing a DNA interstrand cross-link (FIG. 2A). If the same reactive intermediate is formed in an SSRP-bound lesion, then the labile ligand is displaced by a proximal nucleophile on the protein, affording a stable protein-DNA cross-link (FIG. 2B). It is presumed that these pathways can proceed through labilization of either of the two platinum-purine bonds in order to account for the reactivity of both guanine bases with dimethyl sulfate following irradiation. S. Kane et al., (1996) 35 *Biochemistry* 2180, the teachings of which are incorporated herein by reference.

The specific cross-link between HMG domain B and cisplatin-modified DNA identified in the present work occurs at a residue located in the extended strand at the amino-terminus of the protein, which lies within the concave surface of the L-shaped HMG domain B polypeptide. The polypeptide strand contains four proline residues, which may play some role in constraining the conformation of this region. Teo et al. (1995), 230 *Env. J. Biochem.* 943. Significantly, the studies disclosed herein reveal that the N-terminus of domain B must interact with the major groove of the DNA, whereas the α-helices of the domain lie along the minor groove surface. This conclusion is supported by the observed cross-linking of platinum bound to adjacent guanosine residues with Lys-6 of domain B, since the guanine N-7 atoms are located in the major groove of DNA. This result is surprising and unexpected in that, as discussed above, the platinum atom of a cisplatin-type genomic lesion is situated on a DNA surface (the major groove of duplex DNA) opposite to the surface at which the HMG protein binds to the genomic lesion (i.e., the minor groove side). It was not previously appreciated that HMG proteins bound to one side of a lesioned duplex DNA could wrap or curl around the duplex so as to be accessible for participation in covalent bonds on the opposite side of the double helix.

It should be noted, however, that the reported NMR solution structure of the Lef-1 domain bound to its target DNA sequence includes a site at which the polypeptide curls toward the major groove. Love et al. (1995), 376 *Nature* 791. In this structure, the highly basic C-terminal region was found to contact the major groove, crossing over the sugar-phosphate backbone. The N-terminal strand and helix 3 were packed against one another in the minor groove. In HMG domain B, it is the N-terminus that contains a significant number of basic amino acid residues. It is now appreciated, as a result of the studies presented herein, that similar helix packing against the DNA may be a general, sequence-independent feature of HMG domain SSRP protein binding to DNA.

U.S. Pat. No. 5,359,047 describes the identification and characterization of SSRPs and the identification and isolation of nucleic acid fragments encoding SSRPs. Several overlapping human SSRP sequences have been aligned as a composite sequence, reconstructing the complete coding sequence for human SSRP1 (Seq. ID No. 1), also reported also in Bruhn et al. (1992), 89 *Proc. Natl. Acad. Sci. USA* 2307, the teachings of which are incorporated herein by reference. The composite nucleic acid sequence, spanning 2839 bp of DNA, comprises a continuous open reading frame of 2310 bp, extending from nucleotide position 275. This open reading frame encodes a protein, human SSRP1, predicted to have the amino acid sequence set forth in Seq. ID No. 2. Amino acid residues 539 to 614 comprise the HMG domain of SSRP1. This domain shares significant levels of sequence similarity with high mobility group (HMG) 1 and 2 proteins from several eukaryotic species, and with upstream binding factor (UBF), a eukaryotic transcription factor which also contains an HMG domain and activates transcription of ribosomal RNA genes. Jantzen et al. (1990), 344 *Nature* 830; Bustin et al. (1990), 1049 *Biochim. Biophys. Acta* 231; van Holde (1988) *Chromatin* (Springer-Verlag, N.Y.); Eink and Bustin (1985), 156 *Exp. Cell Res.* 295. When optimally aligned, the HMG domains of hSSRP1 and human HMG1 share 47% amino acid identity. Comparable levels of sequence similarity also exist between the hSSRP1 HMG domain and the corresponding regions of other HMG domain proteins, including sex-determining region Y (SRY), mitochondrial transcription factor II (mtTFII), lymphoid enhancer binding factor I (Lef-1), the T-cell specific transcription factor TCF-1α, the yeast autonomously replicating sequence factor ABF2, and a mouse protein, T160, said to bind to V(D)J recombination signal sequence (RSS) probes. Sinclair et al. (1990), 346 *Nature* 240; Gubbay et al. (1990), 346 *Nature* 245; Parisi and Clayton (1991), 250 *Science* 965; Travis et al. (1991), 5 *Genes & Dev.* 880; Waterman et al. (1991), 5 *Genes & Dev.* 656; Diffley and Stillman (1991), 88 *Proc. Natl. Acad. Sci. USA* 7864; Shirakata et al. (1991), 11 *Mol. Cell. Biol.* 4528. Of these, the T160 protein, which shares 95.5% similarity with hSSRP1, is considered to be the murine homolog of human SSRP1. HMG-1 and -2 are strongly evolutionarily conserved, with homologs identified in diverse eukaryotic genomes, including the human, bovine, porcine, rodent, fish, yeast, maize and protozoan genomes. Wen et al. (1989), 17 *Nucl. Acids Res.* 1197; Pentecost and Dixon (1984), 4 *Biosci. Rep.* 49; Kaplan and Duncan (1988), 16 *Nuc. Acids Res.* 10375; Tsuda et al. (1988), 27 *Biochemistry* 6159; Paonessa et al. (1987), 15 *Nucl. Acids Res.* 9077; Lee et al. (1987), 15 *Nucl. Acids Res.* 5051; Pentecost et al. (1985), 13 *Nucl. Acids Res.* 4871; Kolodrubetz and Burgum (1990), 265 *J. Biol. Chem.* 3234; Grasser and Feix (1991), 19 *Nucl. Acids Res.* 2573; Roth et al. (1987), 15 *Nucl. Acids Res.* 8112; Hayashi et al. (1989), 105 *J. Biochem.* 577. HMG-1 and -2 also have been shown to bind specifically to structural distortions in DNA such as B–Z junctions and cruciforms. Bianchi et al. (1989), 243 *Science* 1056; Hamada and Bustin (1985), 24 *Biochemistry* 1428.

Recent studies have established that the HMG-1 protein comprises two domains, each of which is capable independently of binding to four-way junction DNA. Bianchi et al. (1992), 11 *EMBO J.* 1055. This observation confirms earlier reports that HMG-domain fragments of UBF, Lef-1 and TCF-1α retain the specific DNA binding properties of the corresponding intact transcription factors. Jantzen et al. (1990), 344 *Nature* 830; Giese et al. (1991), 5 *Genes & Devel.* 2567; Waterman et al. (1991), 5 *Genes & Dev.* 656. Thus, a single HMG domain is both necessary and sufficient for structure-specific recognition of genomic lesions. This view is supported by reports that human HMG-1 binds strongly and specifically to cisplatin-modified oligonucleotides. Pil and Lippard (1992), 256 *Science* 234; Hughes et al. (1992), 267 *J. Biol. Chem.* 13520.

Giese et al. (1992), 69 *Cell* 185 and King and Weiss (1993), 90 *Proc. Natl. Acad. Sci. USA* 11990, have established that the HMG domain of SRY partially intercalates into the widened minor groove at the apex of the recognized or induced bend in substrate duplex DNA. Bending of DNA by the HMG domain brings into close proximity linearly distant regions of the double helix. HMG-1, UBF, SRY, Lef-1 and related HMG domain proteins accordingly now are viewed as participating in higher ordered aspects of chromatin structure and nuclear architecture. Wolffe (1994), 264 *Science* 1100; King and Weiss (1993), 90 *Proc. Natl. Acad. Sci. USA* 11990; Ferrari et al. (1992), 11 *EMBO J.* 4497 and Giese et al. (1992), 69 *Cell* 185, the teachings of each of which are incorporated herein by reference. These studies confirm the teachings of U.S. Pat. No. 5,359,047 that the 1,2-d(A^G) and 1,2-d(G^G) intrastrand lesions of cisplatin resemble DNA structures that arise naturally within the eukaryotic genome.

As for HMG-1 and -2, homologs of human SSRP1 occur throughout the eukaryotic phyla. Standard Southern blotting techniques involving detectably labeled SSRP DNA as a probe established that gene sequences encoding homologous SSRPs exist at least in chimpanzee, monkey, elephant, pig, dog, rabbit, mouse, opossum, chicken, fish, and the fruitfly, Drosophila melanogaster. The isolation and cloning of the Drosophila SSRP1 homolog are reported in U.S. Pat. No. 5,359,047 and in Bruhn et al. (1993), 21 *Nucl. Acids Res.* 1643, the teachings of which are incorporated by reference herein. Both phylogenetic counterpart proteins include HMG domains at corresponding locations. Thus, homologs or phylogenetic counterparts of the human SSRP1 can be isolated as taught in U.S. Pat. No. 5,359,047 and are suitable for use in the present invention.

Additional useful structure specific recognition proteins can be isolated empirically, based upon their binding to cisplatin-lesioned probe DNA. The yeast structure specific recognition protein, initially referred to as ySSRP (in U.S. Pat. No. 5,359,047) and later as Ixr-1 (intrastrand crosslink recognition protein 1, Brown et al. (1993), 261 *Science* 603), was isolated in this manner.

Accordingly, the DNA structure specific recognition proteins useful in the methods of the present invention comprise at least one HMG domain. Such SSRPs include HMG1, HMG2, UBF, LEF-1, SRY, mtTFA, ABF-2, IXR1 and SSRP. Preferably, the SSRPs used in the methods of the present invention are those SSRPs that are endogenous to and present in cells to be treated according to the present invention.

Eukaryotic cells with which the foregoing methods can be practiced can be cells of a unicellular or multicellular organism. The cells can be maintained in or adapted to culture ex vivo, or can be cells withdrawn from a multicellular organism (e.g., a body fluid sample or tissue biopsy). Alternatively, the cells can be present in vivo in tissue or organs of a multicellular eukaryotic organism. The term, multicellular eukaryotic organism, embraces at least arthropods and vertebrates, including fish, amphibians, birds and mammals, particularly humans. The eukaryotic cells can exhibit normal phenotype or can be turmorigenic (neoplastic or malignant) cells. The methods of the present invention can be practiced with tumorigenic or non-tumorigenic mammalian cells disposed in vivo. Preferably, the tumorigenic mammalian cell is at a tissue surface or is separated from a tissue surface by a photopenetrable depth of intervening tissue and/or is disposed in the skin, retina, gastrointestinal lining, respiratory tract lining or urogenital tract lining. The tumorigenic mammalian cell may be a carcinoma cell or a sarcoma cell. The subject cells are more preferably melanoma, retinoblastoma or cutaneous lymphoma cells; bladder, prostate, endometrial, cervical or vaginal carcinoma cells; colon, buccal, gastric or intestinal carcinoma cells; or laryngeal, tracheal, small cell or non-small cell lung carcinoma cells.

In the methods of the present invention, the subject cells are contacted with a cisplatin-type chemotherapeutic agent to produce a lesion in the genomic DNA of the cell. The cells are then incubated with the genotoxic agent, under conditions known to promote protein-DNA binding, and for a time sufficient to allow an SSRP present in the cell to bind to the genomic lesion to form a non-covalent DNA:protein complex. Those skilled in the art will appreciate that a variety of factors can influence the conditions and time necessary for SSRP binding to the genomic lesion. For example, overexpression of one or more SSRPs within the cell can reduce time necessary for binding to occur. Determiniation of incubation conditions and time sufficient for protein:DNA binding is well within the skill of an ordinarily skilled artisan. The subject cells are then photo-irradiated such that a covalent bond is formed between the SSRP and the genomic lesion. The formation of a covalent bond between the SSRP and the genomic lesion can be monitored by techniques well-known to those skilled in the art, e.g., as demonstrated below in the Examples. The photo-irradiation is preferably carried out using ultraviolet light. It is preferable to irradiate the cells with light having a wavelength of 300 to 1,000 nm, more preferably 300 to 365 nm, still more preferably about 300 nm and most preferably with light having a wavelength of 302 nm. Such photo-irradiation can be carried out by a variety of means well-known in the art, including, for example, using a mercury lamp, a transilluminator or a laser. Furthermore, the practitioner will appreciate that there are a variety of medical devices and endoscopic techniques available to facilitate photo-irradiation of cells.

The present invention also encompasses compositions prepared by the methods described above. Covalently-bound DNA:protein complexes are produced by contacting a cell with a chemotherapeutic agent to produce a genomic lesion in the DNA of the cell, then incubating the cell to provide sufficient time for an SSRP to bind to the lesion and form a non-covalent DNA:protein complex, and finally, the cell (and complex) are photo-irradiated to form a covalent bond between the SSRP and the lesion. Compositions prepared in this manner are comprised of a DNA SSRP (preferably having at least one HMG domain) that is tethered covalently to double-stranded DNA via covalent bonds to a platinum atom linking the SSRP to the DNA. As established in U.S. Pat. No. 5,705,334, incorporated herein by reference, and as discussed above, the DNA:SSRP complex is resistant to cellular repair mechanisms. One of ordinary skill in the art will appreciate that standard cytotoxicity assays can be employed to establish the increased potency of the present covalently-bound complexes.

Practice of the invention will be still more fully understood from the following examples, which are presented herein for illustration only and should not be construed as limiting the invention in any way.

EXAMPLE 1
Photo-Cross-Linking of Platinated DNA Probes to HMG1 and HMG Domain B.

A 123-bp DNA fragment was obtained by digestion of a commercially available 123-bp DNA ladder (Gibco BRL) with restriction enzyme AvaI and purification of the resulting DNA fragment by native polyacrylamide gel electrophoresis (PAGE). The resulting DNA fragment was 3'-end labeled by a fill-in reaction with the Klenow fragment of DNA polymerase I, [$\alpha$-$^{32}$P]dCTP (Dupont/NEN), and the four deoxynucleotide triphosphates, and was purified on a Sephadex G-50 Quick Spin column (Boehringer Mannheim). The diaqua derivatives of the platinum compounds were employed for platination of DNA owing to the low solubility of the compounds in aqueous media (Hartwig et al. (1992) 114 *J. Am. Chem. Soc.* 5646–5654). Platination of DNA was carried out at a formal drug-to-nucleotide ration ($r_f$) of 0.025 by treating a 150 $\mu$M (nucleotide concentration) solution of the 123-bp DNA fragment in 10 mM sodium phosphate, pH 6.8, containing 1×10$^6$ cpm of the labeled DNA with the diaqua derivatives of the platinum compounds at 37° C. for 18 h. Unbound platinum was removed by ethanol precipitation. To determine the amount of metal incorporated, calf thymus DNA was modified under similar conditions and the amount of bound platinum was quantitated by flameless atomic absorption spectroscopy (supporting information). An 82-bp DNA fragment was prepared by 5'-end labeling the unplatinated 123-bp probe with T4 polynucleotide kinase and [$\gamma$-$^{32}$P]ATP (Dupont/NEN) followed by digestion with restriction enzyme HaeIII and purification of the resulting singly end-labeled fragment by native PAGE. The product was platinated at an $r_f$ of 0.036 as described above. A 15-mer, d(CCTCTCTGGTTCTTC) (Seq. ID No. 3), was platinated as described above to afford an oligonucleotide containing a single, site-specific cis-[Pt(NH$_3$)$_2$\{d(GpG)-N(1),-N7(2)\}] intrastrand cross-link. The product, hereafter referred to as 15Pt, was purified by anion-exchange HPLC on a Dionex Nucleopac PA-100 column (9×250 mm) with a solvent system of 10 mM ammonium acetate, pH 6.0, in 10% aqueous acetonitrile and a gradient of 0.2–0.35 M NaCl. The HPLC fractions were desalted by extensive dialysis against deionized water (Spectra/Por 7 tubing, 1000 MW cutoff, from Spectrum). The sites of platination were confirmed by Maxam-Gilbert sequencing analysis (Comess et al. (1990) 29 *Biochemistry* 2102–2110; Brabec et al. (1993) 90 *Proc. Natl. Acad. Sci. USA* 5345–5349). The bottom strand 15-mer (15B) was purified by denaturing PAGE. Oligonucleotides were 5'-end labeled with T4 polynucleotide kinase and [$\gamma$-$^{32}$P]ATP and purified on Sephadex G-25 Quick Spin columns.

Reaction mixtures (10 $\mu$L total volume) were prepared containing 10 mM Tris-HCl, pH 7.5, 4% (v/v) glycerol, 10 mM MgCl2, 50 mM KCl, 1 mM EDTA and 0.05% (v/v) Nonidet P-40. HMG domain B [expressed and purified from pHB1/*Escherichia coli* BL21 (DE3) (Chow et al. (1995) *Biochemistry* 33: 15124–30)] was added, and the solution was incubated for 30 min on ice to allow protein-DNA binding. For binding of the 123- and 82-bp probes to HMG1, 0.2 $\mu$g of BSA/mL, 2 $\mu$g of competitor chicken erythrocyte DNA, and 300 ng of HMG1 were included in the reaction mixtures. To induce photo-cross-linking of the protein—DNA complexes, the reaction mixtures contained in open microcentrifuge tubes were placed on ice and irradiated from about for 1–2 h at a distance of 4 cm from a transilluminator (Ultra-Violet Products, TM-15) equipped with one of several different lamps, with primary spectral outputs of 254, 302, or 365 nm. The light intensity, 2.6–2.9 J m$^{-2}$ s$^{-1}$, was measured with a UVX radiometer (Ultra-Violet Products). Following irradiation, the reaction mixtures were combined with 5 $\mu$L of gel-loading solution [10 M urea, 1.5 mM EDTA, 0.05% (w/v) bromophenol blue and xylene cyanol]. The DNA was denatured by heating at 90° C. for 4 min and then analyzed by denaturing PAGE. The denaturing 8% polyacrylamide gel was run to determine photo-crosslinking of HMG1 to globally platinated 123-bp probes. Lanes 1–3 contained unplatinated probe. Lanes 4–6 contained cisplatin-modified probe. Lanes 7–9 contained Pt-$L_4$-modified probe. Lanes 10–12 contained Pt-$L_6$-modified probe. Lanes 13–15 contained Pt-$L_8$-modified probe. Lanes 1, 4, 7, 10 and 13 contained DNA alone. Lanes 2, 5, 8, 11 and 14 contained samples irradiated in the absence of protein. Lanes 3, 6, 9, 12 and 15 were incubated with 300 ng of HMG1 and then irradiated. The gels were visualized by autoradiography at −80° C. All lanes showed a rapidly migrating band of unattached probe. Lanes 5, 8, 11 and 14 showed a pair of relatively slowly migrating bands identified as interstrand cross-linked DNA. Lanes 6, 12 and 15 showed a slowly migrating band identified as cross-linked DNA-protein complex.

The presence of a slowly migrating species (lanes 9, 12 and 15) indicated the formation of covalently cross-linked protein-DNA complexes. Use of a cisplatin-modified probe (lane 6), revealed significantly more efficient photo-cross-inking to HMG1 than any of the DNA probes platinated with the aryl azide complexes. In the absence of protein, other bands appeared having mobilities slower than that of single-stranded DNA (lanes 5, 8, 11, and 14); these bands were tentatively assigned to DNA containing interstrand cross-links. The presence of more than one such band may represent DNA duplexes containing different numbers and kinds of cross-links, resulting in mixtures of partially and fully denatured species with differing gel mobilities.

EXAMPLE 2
Wavelength Dependence of the Photo-Cross-linking Reaction.

To gain insight into the mechanism of the photo-cross-linking reaction, the dependence of the reaction on the wavelength of irradiation was examined. A denaturing 6% polyacrylamide gel was run to determine wavelength dependence of the photoreactivity of cisplatin-modified 82-bp DNA. Lanes 1–3, 7–9 and 13–15 contained unplatinated probe. Lanes 4–6, 10–12 and 16–18 contained cisplatin-modified probe. Lanes 1, 4, 7, 10, 13 and 16 contained DNA alone. Lanes 2, 3, 5 and 6 were irradiated with 254 nm light. Lanes 8, 9, 11 and 12 were irradiated with 302 nrn light. Lanes 14, 15, 17 and 18 were irradiated with 365 nm light. HMG1 (300 ng) was present in the samples run at lanes 3, 6, 9, 12, 15 and 18.

Lanes 5 and 6 showed rapidly migrating bands identified as fragmented DNA. Lanes 2, 3, 5, 6, 11, 12, 16 and 17 showed slower migrating bands identified as DNA with interstrand crosslink(s). Lanes 6 and 12 showed a slowly migrating band identified as cross-linked DNA-protein.

The results indicated that 254 nm light promotes the formation of DNA interstrand cross-links and protein-DNA cross-links with the cisplatin-modified probe (lanes 1–6), but unplatinated DNA was also reactive under these conditions. Furthermore, 254 nm light caused significant photogradation of both unplatinated and platinated probes, as evidenced by the appearance of DNA fragments at the bottom of the gel. Irradiation of the cisplatin-modified probe with 302 nm light (lanes 7–12) caused both DNA interstrand cross-linking protein-DNA cross-linking in the presence of HMG1. Unplatinated probe did not react under these conditions. Both probes were unreactive when irradiated with 365 nm light. The 302 nm wavelength light was therefore used in all subsequent experiments.

The use of a medium-pressure mercury lamp emitting over a broad spectral range (300–1000 nm) also promoted protein-DNA cross-linking but less efficiently than light at 302 nm from the transilluminator.

EXAMPLE 3
Photoreactivity of DNA Modified with cis-DDP, trans-DDP, [Pt(dien)Cl]Cl, and [Pt(NH$_3$)$_3$Cl]Cl.

The specificity of the photo-cross-linking reaction was assessed by comparing the photoreactivity of DNA modified with different platinum compounds. A denaturing 6% polyacrylamide gel was run to determine the photoreactivity of various 82-bp platinated probes. Lanes 1–3 contained unplatinated DNA. Lanes 4–6 contained cisplatin-modified DNA. Lanes 7–9 contained DNA modified with trans-DDP. Lanes 10–12 contained DNA modified with [Pt(dien)Cl]Cl. Lanes 13–15 contained DNA modified with [Pt(NH$_3$)$_3$Cl]Cl. Lanes 1, 4, 7, 10 and 13 contained DNA alone. Lanes 2, 5, 8, 11 and 14 contain samples irradiated in the absence of protein. Lanes 3, 6, 9, 12 and 15 contained samples incubated with 300 ng of HMG1 and then irradiated.

All lanes showed a rapidly migrating band of unattached probe. Lanes 5 and 6 showed very dark bands that were slower migrating and identified as interstrand cross-linked DNA. Corresponding bands in the other lanes were very faint. Lane 6 also showed a slowly migrating band identified as cross-linked DNA-protein complex.

DNA containing cis-DDP adducts were highly reactive when irradiated with 302 nm light, producing both DNA interstrand cross-links and protein-DNA cross-links in the presence of HMG1 (lanes 5 and 6). DNA containing trans-DDP adducts (lanes 7–9) or platinum monoadducts (lanes 10–15) did not photo-cross-link to HMG1 upon irradiation and produced only small amounts of the DNA interstrand cross-links. In a separate experiment, DNA modified with [Pt(en)Cl$_2$] underwent photoinduced DNA interstrand cross-linking and cross-linking to HMG1, although with about half the efficiency as the cis-DDP modified probe. These results demonstrate that the light-driven reactions are unique to DNA modified with platinum compounds containing two cis amine ligands bound in a bifunctional manner.

EXAMPLE 4
Photo-Cross-linking of a Site-Specifically Platinated 15-bp DNA Duplex to HMG Domain B.

Studies were carried out to identify the site(s) of protein cross-linking by cisplatin modified DNA. The studies employed the smallest system capable of modeling the interaction of HMG1 with binds specifically to oligonucleotides containing a single cis-DDP intrastrand d(GpG) cross-link, in the same specific manner as HMG1 binds to longer platinated DNA probes (Chow et al. (1995), *Biochemistry* 33: 15124–30). Accordingly, a 15-base oligonucleotide containing a single cis-[Pt(NH$_3$)$_2${d(GpG)-N7(1),-N7(2)}] intrastrand adduct (15Pt) was prepared and hybridized to its complement (15B), and the interaction of the corresponding duplex with HMG domain B was characterized in a gel mobility shift assay. A native 10% polyacrylamide gel was run in which: lanes 1–5 contained unplatinated DNA; lanes 6–10 contained cisplatin-modified DNA; lanes 11–15 contained single-stranded cisplatin-modified oligonucleotide; lanes 1, 6 and 11 contain samples with no protein; while lanes 2–5, 7–10 and 12–15 contain 10, 20, 30 and 40 equivalents of HMG domain B, respectively. All lanes showed a rapidly migrating band of unbound probe, while lanes 7–10 showed a more slowly migrating band identified as HMG domain B bound to the platinated duplex. Domain B bound specifically and efficiently to the platinated duplex (lanes 7–10), the amount of bound DNA increasing as the protein concentration increased. Binding to unplatinated or single-stranded DNA control substrates was not observed.

The ability of the platinated 15-bp duplex to photo-cross-link to HMG domain B was next investigated. Protein-DNA mixtures were equilibrated, irradiated, and then analyzed by denaturing gel electrophoresis. The denaturing 8% polyacrylamide gel included lanes 1–4 which contained unplatinated DNA; lanes 5–10 which contained cisplatin-modified DNA. Lanes 1 and 5 contained DNA alone. Lanes 2 and 6 contained 40 equivalents of HMG domain B. Lanes 3 and 7 were irradiated, but contained no protein. Lanes 4 and 8–10 were incubated with 40 equivalents of HMG domain B and then irradiated. Lane 9 was irradiated and then treated with 0.2 M NaCN, pH 8.5. Lane 10 was irradiated then treated with 0.1 mg of proteinase K/mL.

All lanes showed a rapidly migrating band identified as unbound probe. Lanes 6–10 showed a less rapidly migrating band identified as interstrand cross-linked DNA. Lanes 8 and 9 showed a slowly migrating band identified as cross-linked DNA-protein complex.

Irradiation of the platinated DNA in the absence of protein resulted in interstrand cross-linked DNA (lane 7). In the presence of HMG domain B, a slowly migrating band was observed (lane 8) which was reversed following NaCN treatment (lane 9) and digestion with proteinase K (lane 10). Treatment of the cross-linked protein-DNA complex with proteinase K produced a cluster of bands that migrated slightly more slowly than the free oligonucleotide. These new bands presumably contain platinated oligonucleotide attached to short peptide fragments of HMG domain B; it is likely that platinum binding blocked the protease, preventing complete digestion. No cross-linking was seen for unirradiated reaction mixtures. Also of interest is that the uncross-linked starting material remaining in lanes 7–10 migrated slightly faster than platinated oligonucleotide that had not been irradiated (lane 6) but slower than unplatinated oligonucleotide (lane 1). This result suggests perhaps that platinum is no longer bound bifInctionally after irradiation (vide infra).

Experiments were carried out to demonstrate that the most slowly migrating species corresponds to material containing platinum-induced DNA-protein cross-links. Reaction mixtures containing HMG1 and DNA probe modified by cis-DDP were irradiated. Subsequent incubation with NaCN under conditions which reverse platinum-DNA adducts (Comess & Lippard, (1993) in *Molecular Aspects of Anticancer Drug-DNA Interactions* (S. Neidle et al., Eds.) pp. 134, MacMillan, London), or with proteinase K, eliminated bands containing the presumed protein-DNA cross-linked species, converting them to that of the unmodified probe. The protein-platinated DNA cross-links could also be reversed with sulfur-containing nucleophiles such as thiourea and β-mercaptoethanol. These results demonstrate that the protein-DNA cross-links form in a novel reaction of the platinum complex, not from the more commonly encountered direct photochemical linking of a nucleobase to an amino acid (Sheltar, (1980) *Photochem. Photobiol. Rev.* 5: 105).

Bands assigned to interstrand cross-linked DNA were also absent following NaCN, but not proteinase K, treatment. This result provides good evidence that these species also resulted from platinum-mediated reactions and not from nonspecific photochemical cross-linking, for example, to the carrier protein bovine serum albumin (BSA) in the reaction medium. Moreover, the fact that carrier BSA did not cross-link to the platinated DNA under any condition suggests that the cross-link to HMG1 occurred only after formation of a specific non-covalent complex with this protein.

EXAMPLE 5

Determination of the Photo-Cross-Linked Amino Acid in HMG Domain B.

The site of cross-linking in HMG domain B was determined in the following manner. The volume of the photo-cross-linking reaction mixture was scaled up by several orders of magnitude to facilitate the generation of sufficient material for these experiments. Aliquots of this reaction mixture, containing cross-linked and free HMG domain B, were employed for digestion with different proteases. The resulting proteolyzed complexes were purified on denaturing gels and then analyzed by N-terminal amino acid sequencing. The point of interruption of the corresponding peptide sequence indicates the exact position of attachment. This methodology has been previously employed to identify UV-cross-linked sites of single-stranded DNA binding proteins (Merrill et al., (1984) *J. Biol. Chem.* 259: 10850–56), contacts between integration host factor and its DNA target (Yang & Nash, (1994) *Proc. Nat'l Acad. Sci. USA* 91: 12183–87), and amino acid residues at the DNA binding site of *E. coli* uracil DNA glycosylase (Allen et al., (1991) *J. Biol. Chem.* 266: 6113–19).

A. Large-Scale Preparation and Purification of Photo-Cross-linked 15Pt-HMG Domain B Complex.

Reaction mixtures like those described in Example 1 were scaled up to 100 mL volumes by using 100 nmol of 15-bp duplex and 150 nmol of HMG domain B. Gel mobility shift assays at this DNA concentration (1 $\mu$M) demonstrated that the addition of 1.5 equiv of HMG domain resulted in platinum-specific DNA binding, with ~50% of the DNA shifting to the bound fraction. Addition of more protein or the use of higher DNA concentrations resulted in mixtures of specific and non-specific complexes, readily distinguishable by gel electrophoresis, and was therefore avoided. The protein-DNA binding mixture was incubated on ice for 30 min prior to irradiation for 2 h as described above. The solution volume was subsequently reduced to 2 mL by using Centriplus-10 concentrators (Amicon). The complexes were precipitated by addition of 4 vol of ice-cold acetone and collected by centrifngation. The precipitate was redissolved in 10 mM Tris-HCl, pH 8.0, containing 50 mM NaCl and 10 mM $MgCl_2$ and was used in the protease digestions described below. For each of the digestions, the yield of total products was approximately 10–15% of the initial amount of oligonucleotide employed.

B. Protease Digestions of Photo-Cross-Linked 15Pt-HMG Domain B Complex:

(1) Endoproteinase Asp-N Digest.

The mixture of cross-linked and free HMG domain B containing 30 nmol of duplex DNA and 45 nmol (420 μg) of protein was digested with 4 μg of endoproteinase Asp-N (Sigma, sequencing grade) in 420 μL total volume of 50 mM Tris-HCl buffer pH 8.5. The reaction mixture was incubated at 37° C. for 4 h, and then concentrated to 100 μL in a Microcon-3 concentrator (Amicon). The mixture was combined with 50 μL of gel-loading solution [10 M urea, 1.5 mM EDTA, 0.05% (w/v) bromophenol blue and xylene cyanole], heat-denatured, and then purified on a 12% polyacrylamide/7 M urea gel (1.5 mm thick). A control, consisting of full length (undigested) complex and probe was also run. The gel was visualized by UV shadowing and autoradiography. The gel showed a rapidly migrating band that was identified as free probe, as well as a slowly migrating band identified as the full length complex. An intermediate, slowly migrating band was identified as incomplete digestion of the isolated products (confirmed by more extensive endoproteinase treatment). Two closely spaced bands corresponding to protease-digested material were observed. These bands were excised from the gel, and the DNA-peptide complexes were recovered by passive elution into 10 mM Tris-HCl, pH 7.5. containing 50 mM NaCl and 1 mM EDTA. The eluates were filtered (0.2 μm microfilterfuge tubes, Rainin) to remove gel pieces and then desalted on gel filtration columns (PD-10, Pharmacia) pre-equilibrated with water and then lyophilized to dryness. Approximately 1.5 nmol of each product (corresponding to the "upper" and "lower" migrating bands) were isolated, as determined by the $A_{260}$ for the oligonucleotide.

(2) Endoproteinase Arg-C Digest.

The mixture of cross-linked and free HMG domain B containing 20 nmol of duplex DNA and 30 nmol (280 μg) of protein was digested with 2 μg of endoproteinase Arg-C (Boehringer Mannheim, sequencing grade) in a solution 300 μL total volume) containing 50 mM Tris-HCl, pH 7.5, 5 mM dithiothreitol, and 5 mM $CaCl_2$. The mixture was incubated at 37° C. for 8 h, after which time an additional 2 μg aliquot of protease was added, and the solution was incubated overnight at 37° C. The mixture was concentrated, and the peptide -DNA complex was purified and run on a gel, as described above. The gel showed a rapidly migrating band identified as free probe, and a slowly migrating band (full length complex). Only one band corresponding to protease-digested material was observed. The band was excised from the gel, and the DNA-peptide complex was recovered and desalted as described above to afford approximately 3 nmol of product. N-terminal sequencing analysis was performed by the MIT Biopolymers Laboratory.

Edman degradation of the isolated peptides cross-linked to the platinated oligonucleotide yielded a single amino acid sequence which, in each case, matched that of a portion of the known sequence of HMG domain B (Table 1). For both of the Asp-N protease fragments, the MKKKF sequence (Seq. ID No. 4) obtained precisely matched that of the first five amino acids from the N-terminus of domain B. Comparison of this sequence with that predicted from the protease specificity revealed that the sixth amino acid, a lysine, did not appear as expected (Table 1). Noteworthy is the fact that, although these two peptide fragments afforded the same exact amino acid sequence, they had slightly different gel mobilities. This result may reflect subtle differences in the two products, such as differential placement of the platinum ligands following irradiation. The endoproteinase Arg-C digest yielded a peptide matching residues 1–12 of domain B with an interruption in the sequence at cycle six. As a control, the full-length unmodified HMG domain B was also subjected to Edman degradation and did not show any interruptions in its amino acid sequence. The absence of any detectable amino acid at cycle six and a decrease in the yields for all subsequent cycles indicate that, by analogy to other types of cross-linked protein-DNA complexes reported previously (Yang & Nash, (1994) *Proc. Nat'l Acad. Sci. USA* 91: 12183–87), the amino acid which becomes cross-linked to the platinated oligonucleotide is Lys-6 of HMG domain B.

TABLE 1

Amino Acid Sequences of Proteolyzed Cross-Linked Peptide Complexes of Platinated DNA

| peptide fragment | N-terminal sequence* | expected fragment on the basis of protease specificity |
|---|---|---|
| Asp-N, upper | MKKKF(--)[1] | MKKKFK[4] |
| Asp-N, lower | MKKKF(--)[1] | MKKKFK[4] |
| Arg-C | MKKKF(--)DPNAPK[2] | MKKKFKDPNAPKR[5] |
| full HMG domain B | MKKKFKDPN[3] | |

*The symbol "(--)" denotes a sequencing cycle in which no amino acid was detected, ostensibly because the cross-linked platinated DNA altered its usual HPLC mobility.
[1]Seq. ID No. 4.
[2]Seq. ID No. 5.
[3]Seq. ID No. 6.
[4]Seq. ID No. 7.
[5]Seq. ID No. 8.

Equivalents

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A method for potentiating cytotoxicity of a chemotherapeutic agent that inflicts genomic lesions on cellular DNA, comprising the steps of:
   (a) contacting a eukaryotic cell with said chemotherapeutic agent, such that said agent produces a genomic lesion in DNA of said cell;
   (b) incubating said cell in the presence of said agent for a time sufficient for a structure-specific DNA recognition protein present in said cell to bind to the genomic lesion produced by said agent, forming a non-covalent DNA:protein complex; and
   (c) photo-iradiating said complex, such that a covalent bond is formed therein between said structure-specific DNA recognition protein and said genomic lesion.

2. The method of claim 1 wherein said chemotherapeutic agent forms a genomic lesion comprising a covalent 1,2-intrastrand dinucleotide adduct of said agent.

3. The method of claim 2 wherein said chemotherapeutic agent forms a genomic lesion comprising a covalent 1,2-intrastrand d(ApG) or d(GpG) adduct of said agent.

4. The method of claim 1, 2 or 3 wherein said DNA structure-specific recognition protein comprises at least one HMG domain.

5. The method of claim 4 wherein said DNA structure-specific recognition protein is selected from the group consisting of HMG1, HMG2, UBF, LEF-2, SRY, mtTFA, ABF2, IXR1 and SSRP.

6. The method of claim 4 wherein said chemotherapeutic agent is a metal coordination compound.

7. The method of claim 6 wherein said metal coordination compound is a platinum compound.

8. The method of claim 7 wherein said platinum compound is a platinum(II) or platinum(IV) compound comprising a platinum atom linked covalently to a pair of cis configured substitutionally labile moieties and a pair of cis configured electron donor moieties.

9. The method of claim 8 wherein said platinum compound is cisplatin, carboplatin or iproplatin.

10. The method of claim 4 wherein said photo-irradiation step is carried out using ultraviolet light.

11. The method of claim 10 wherein said photo-irradiation step is carried out using a mercury lamp.

12. The method of claim 10 wherein said photo-irradiation step is carried out by irradiating said cell with light having a wavelength of 300 to 1000 nm.

13. The method of claim 12 wherein said photo-irradiation step is carried out by irradiating said cell with light having a wavelength of 300 to 365 nm.

14. The method of claim 13 wherein said photo-irradiation step is carried out by irradiating said cell with light having a wavelength of about 300 nm.

15. The method of claim 14 wherein said photo-irradiation step is carried out by irradiating said cell with light having a wavelength of 302 nm.

16. The method of claim 4 wherein said eukaryotic cell is a mammalian cell disposed in vivo in a mammal.

17. The method of claim 16 wherein said eukaryotic cell is a tumorigenic mammalian cell disposed in vivo in a mammal.

18. The method of claim 17 wherein said tumorigenic mammalian cell is disposed in skin, retina, gastrointestinal lining, respiratory tract lining, or urogenital tract lining.

19. The method of claim 17 wherein said tumorigenic mammalian cell is at a tissue surface or is seperated from a tissue surface by photopenetrable depth of intervening tissue.

20. The method of claim 17 wherein said tumorigenic mammalian cell is a carcinoma cell or a sarcoma cell.

21. The method of claim 18 wherein said tumorigenic mammalian cell is a melanoma, retinoblastoma or cutaneous lymphoma cell.

22. The method of claim 18 wherein said tumorigenic mammalian cell is a bladder, prostate, endometrial, cervical or vaginal carcinoma cell.

23. The method of claim 18 wherein said tumorigenic mammalian cell is a colon, buccal, gastic or intestinal carcinoma cell.

24. The method of claim 18 wherein said tumorigenic mammalian cell is a laryngeal, tracheal, small cell or non-small cell lung carcinoma cell.

25. A method for potentiating cytotoxicity of a platinum coordination compound that inflicts genomic lesions on mammalian cellular DNA, said genomic lesions comprising 1,2-intrastrand dinucleotide adducts of said platinum coordination compound, said method comprising the steps of:
   (a) contacting a tumorigenic mammalian cell with said platinum cooridination compound, such that said a genomic lesion is produced in DNA of said tumorigenic cell;
   (b) incubating said tumorigenic cell in the presence of said compound for a time sufficient for a DNA structure-specific recognition protien comprising at least one HMG domain to bind to said genomic lesion, forming a non-covalent DNA:protein complex; and
   (c) photo-irradating said complex, such that a covalent bond is formed therein, tethering said protein to said genomic lesion.

26. A method for potentiating cytotoxicity of a platinum coordination compound selected from the group consisting of cisplatin, iproplatin and carboplatin, said method comprising the steps of:
   (a) contacting a tumorigenic mammalian cell with said platinum coordination compound, such that a platinated genomic lesion is produced in DNA of said tumorigenic cell;

(b) incubating said tumorigenic cell in the presence of said compound for a time sufficient for an HMG domain protein to bind to said genomic lesion, forming a non-covalent DNA:protein complex; and (c) photo-irradiating said complex with ultraviolet light having a wavelength of about 300 nm, such that a covalent bond is formed in said complex, tethering said HMG domain protein to said genomic lesion.

27. A DNA:protein complex comprising a structure-specific DNA recognition protein bound via a covalent crosslink to a genomic lesion in DNA, said genomic lesion being produced by a chemotherapeutic agent.

28. The DNA:protein complex of claim 27 wherein said genomic lesion comprises a covalent 1,2-intrastrand dinucleotide adduct of said chemotherapeutic agent.

29. The DNA:protein complex of claim 28 wherein said genomic lesion comprises a covalent 1,2-intrastrand d(ApG) or d(GpG) adduct of said chemotherapeutic agent.

30. The DNA:protein complex of claim 27 wherein said DNA structure-specific recognition protein comprises at least one HMG domain.

31. The DNA:protein complex of claim 30 wherein said DNA structure-specific recognition protein is selected from the group consisting of HMG1, HMG2, UBF, LEF-1, SRY, mtTFA, ABF2, IXR1 and SSRP.

32. The DNA:protein complex of claim 30 wherein said chemotherapeutic agent is a meetal coordination compound.

33. The DNA:protein complex of claim 32 wherein said metal coordination compound is a platinum compound.

34. The DNA:protein complex of claim 33 wherein said platinum compound is a platinum (II) or platinum(IV) compound comprising a platinum atom linked covalently to a pair of cis configured substitutionally labile moieties and a pair of cis configured electron donor moieties.

35. The DNA:protein complex of claim 34 wherein said platinum compound is cisplatin, carboplatin or ibroplatin.

36. The DNA:protein complex of claim 27 wherein said covalent crosslink is formed by photo-irradiation of said complex.

37. The DNA:protein complex of claim 36 wherein said covalent crosslink is formed by photo-irradiation of said complex with ultraviolet light.

38. The DNA:protien complex of claim 37 wherein said ultraviolet light has a wavelength of about 300 to 365 nm.

39. The DNA:protein complex of claim 38 wherein said ultraviolet light has a wavelength of about 302 nm.

40. A covalent DNA:protein complex produced according to the method of claim 1, 25 or 26.

41. A composition comprising a DNA structure-specific recognition protein tethered covalently to double-stranded DNA via covalent bonds to a platinum atom linking said protein to said DNA.

42. The composition of claim 41 wherein said DNA structure-specific recognition protein comprises at least one HMG domain.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
       (A) LENGTH: 2839 base pairs
       (B) TYPE: nucleic acid
       (C) STRANDEDNESS: double
       (D) TOPOLOGY: linear (ii) MOLECULE TYPE: cDNA (vi) ORIGINAL SOURCE:
       (A) ORGANISM: Homo sapiens (vii) IMMEDIATE SOURCE:
       (B) CLONE: human SSRP - composite of six overlapping
           cDNA clones (viii) POSITION IN GENOME:
       (A) CHROMOSOME/SEGMENT: 11q12

(ix) FEATURE:
       (A) NAME/KEY: CDS
       (B) LOCATION: 275..2401

(xi) SEQUENCE DESCRIPTION: SEQ ID NO:1:

```
GAATTCCGTA CGGCTTCCGG TGGCGGGACG CGGGGCCGCG CACGCGGGAA AAGCTTCCCC      60

GGTGTCCCCC CATCCCCCTC CCCGCGCCCC CCCCGCGTCC CCCCAGCGCG CCCACCTCTC     120

GCGCCGGGGC CCTCGCGAGG CCGCAGCCTG AGGAGATTCC CAACCTGCTG AGCATCCGCA     180

CACCCACTCA GGAGTTGGGG CCCAGCTCCC AGTTTACTTG GTTTCCCTTG TGCAGCCTGG     240

GGCTCTGCCC AGGCCACCAC AGGCAGGGGT CGAC ATG GCA GAG ACA CTG GAG        292
                                     Met Ala Glu Thr Leu Glu
                                       1               5

TTC AAC GAC GTC TAT CAG GAG GTG AAA GGT TCC ATG AAT GAT GGT CGA       340
Phe Asn Asp Val Tyr Gln Glu Val Lys Gly Ser Met Asn Asp Gly Arg
            10              15                  20

CTG AGG TTG AGC CGT CAG GGC ATC ATC TTC AAG AAT AGC AAG ACA GGC       388
Leu Arg Leu Ser Arg Gln Gly Ile Ile Phe Lys Asn Ser Lys Thr Gly
        25                  30                  35

AAA GTG GAC AAC ATC CAG GCT GGG GAG TTA ACA GAA GGT ATC TGG CGC       436
Lys Val Asp Asn Ile Gln Ala Gly Glu Leu Thr Glu Gly Ile Trp Arg
    40                  45                  50

CGT GTT GCT CTG GGC CAT GGA CTT AAA CTG CTT ACA AAG AAT GGC CAT       484
Arg Val Ala Leu Gly His Gly Leu Lys Leu Leu Thr Lys Asn Gly His
55                  60                  65                  70

GTC TAC AAG TAT GAT GGC TTC CGA GAA TCG GAG TTT GAG AAA CTC TCT       532
Val Tyr Lys Tyr Asp Gly Phe Arg Glu Ser Glu Phe Glu Lys Leu Ser
                75                  80                  85

GAT TTC TTC AAA ACT CAC TAT CGC CTT GAG CTA ATG GAG AAG GAC CTT       580
Asp Phe Phe Lys Thr His Tyr Arg Leu Glu Leu Met Glu Lys Asp Leu
            90                  95                 100

TGT GTG AAG GGC TGG AAC TGG GGG ACA GTG AAA TTT GGT GGG CAG CTG       628
Cys Val Lys Gly Trp Asn Trp Gly Thr Val Lys Phe Gly Gly Gln Leu
        105                 110                 115

CTT TCC TTT GAC ATT GGT GAC CAG CCA GTC TTT GAG ATA CCC CTC AGC       676
Leu Ser Phe Asp Ile Gly Asp Gln Pro Val Phe Glu Ile Pro Leu Ser
    120                 125                 130

AAT GTG TCC CAG TGC ACC ACA GGC AAG AAT GAG GTG ACA CTG GAA TTC       724
```

|     |     |     |     |     |     |     |     |     |     |     |     |     |     |     |      |
|-----|-----|-----|-----|-----|-----|-----|-----|-----|-----|-----|-----|-----|-----|-----|------|
| Asn | Val | Ser | Gln | Cys | Thr | Thr | Gly | Lys | Asn | Glu | Val | Thr | Leu | Glu | Phe  |
| 135 |     |     |     |     | 140 |     |     |     |     | 145 |     |     |     |     | 150  |
| CAC | CAA | AAC | GAT | GAC | GCA | GAG | GTG | TCT | CTC | ATG | GAG | GTG | CGC | TTC | TAC | 772 |
| His | Gln | Asn | Asp | Asp | Ala | Glu | Val | Ser | Leu | Met | Glu | Val | Arg | Phe | Tyr |     |
|     |     |     |     | 155 |     |     |     |     | 160 |     |     |     |     | 165 |     |     |
| GTC | CCA | CCC | ACC | CAG | GAG | GAT | GGT | GTG | GAC | CCT | GTT | GAG | GCC | TTT | GCC | 820 |
| Val | Pro | Pro | Thr | Gln | Glu | Asp | Gly | Val | Asp | Pro | Val | Glu | Ala | Phe | Ala |     |
|     |     |     | 170 |     |     |     |     | 175 |     |     |     |     | 180 |     |     |     |
| CAG | AAT | GTG | TTG | TCA | AAG | GCG | GAT | GTA | ATC | CAG | GCC | ACG | GGA | GAT | GCC | 868 |
| Gln | Asn | Val | Leu | Ser | Lys | Ala | Asp | Val | Ile | Gln | Ala | Thr | Gly | Asp | Ala |     |
|     |     | 185 |     |     |     |     | 190 |     |     |     |     | 195 |     |     |     |     |
| ATC | TGC | ATC | TTC | CGG | GAG | CTG | CAG | TGT | CTG | ACT | CCT | CGT | GGT | CGT | TAT | 916 |
| Ile | Cys | Ile | Phe | Arg | Glu | Leu | Gln | Cys | Leu | Thr | Pro | Arg | Gly | Arg | Tyr |     |
|     | 200 |     |     |     |     | 205 |     |     |     |     | 210 |     |     |     |     |     |
| GAC | ATT | CGG | ATC | TAC | CCC | ACC | TTT | CTG | CAC | CTG | CAT | GGC | AAG | ACC | TTT | 964 |
| Asp | Ile | Arg | Ile | Tyr | Pro | Thr | Phe | Leu | His | Leu | His | Gly | Lys | Thr | Phe |     |
| 215 |     |     |     | 220 |     |     |     |     | 225 |     |     |     |     | 230 |     |     |
| GAC | TAC | AAG | ATC | CCC | TAC | ACC | ACA | GTA | CTG | CGT | CTG | TTT | TTG | TTA | CCC | 1012 |
| Asp | Tyr | Lys | Ile | Pro | Tyr | Thr | Thr | Val | Leu | Arg | Leu | Phe | Leu | Leu | Pro |     |
|     |     |     | 235 |     |     |     |     | 240 |     |     |     |     | 245 |     |     |     |
| CAC | AAG | GAC | CAG | CGC | CAG | ATG | TTC | TTT | GTG | ATC | AGC | CTG | GAT | CCC | CCA | 1060 |
| His | Lys | Asp | Gln | Arg | Gln | Met | Phe | Phe | Val | Ile | Ser | Leu | Asp | Pro | Pro |     |
|     |     | 250 |     |     |     |     | 255 |     |     |     |     | 260 |     |     |     |     |
| ATC | AAG | CAA | GGC | CAA | ACT | CGC | TAC | CAC | TTC | CTG | ATC | CTC | CTC | TTC | TCC | 1108 |
| Ile | Lys | Gln | Gly | Gln | Thr | Arg | Tyr | His | Phe | Leu | Ile | Leu | Leu | Phe | Ser |     |
|     | 265 |     |     |     |     | 270 |     |     |     |     | 275 |     |     |     |     |     |
| AAG | GAC | GAG | GAC | ATT | TCG | TTG | ACT | CTG | AAC | ATG | AAC | GAG | GAA | GAA | GTG | 1156 |
| Lys | Asp | Glu | Asp | Ile | Ser | Leu | Thr | Leu | Asn | Met | Asn | Glu | Glu | Glu | Val |     |
|     | 280 |     |     |     | 285 |     |     |     |     | 290 |     |     |     |     |     |     |
| GAG | AAG | CGC | TTT | GAG | GGT | CGG | CTC | ACC | AAG | AAC | ATG | TCA | GGA | TCC | CTC | 1204 |
| Glu | Lys | Arg | Phe | Glu | Gly | Arg | Leu | Thr | Lys | Asn | Met | Ser | Gly | Ser | Leu |     |
| 295 |     |     |     |     | 300 |     |     |     |     | 305 |     |     |     |     | 310 |     |
| TAT | GAG | ATG | GTC | AGC | CGG | GTC | ATG | AAA | GCA | CTG | GTA | AAC | CGC | AAG | ATC | 1252 |
| Tyr | Glu | Met | Val | Ser | Arg | Val | Met | Lys | Ala | Leu | Val | Asn | Arg | Lys | Ile |     |
|     |     |     |     | 315 |     |     |     |     | 320 |     |     |     |     | 325 |     |     |
| ACA | GTG | CCA | GGC | AAC | TTC | CAA | GGG | CAC | TCA | GGG | GCC | CAG | TGC | ATT | ACC | 1300 |
| Thr | Val | Pro | Gly | Asn | Phe | Gln | Gly | His | Ser | Gly | Ala | Gln | Cys | Ile | Thr |     |
|     |     |     | 330 |     |     |     |     | 335 |     |     |     |     | 340 |     |     |     |
| TGT | TCC | TAC | AAG | GCA | AGC | TCA | GGA | CTG | CTC | TAC | CCG | CTG | GAG | CGG | GGC | 1348 |
| Cys | Ser | Tyr | Lys | Ala | Ser | Ser | Gly | Leu | Leu | Tyr | Pro | Leu | Glu | Arg | Gly |     |
|     |     | 345 |     |     |     |     | 350 |     |     |     |     | 355 |     |     |     |     |
| TTC | ATC | TAC | GTC | CAC | AAG | CCA | CCT | GTG | CAC | ATC | CGC | TTC | GAT | GAG | ATC | 1396 |
| Phe | Ile | Tyr | Val | His | Lys | Pro | Pro | Val | His | Ile | Arg | Phe | Asp | Glu | Ile |     |
|     | 360 |     |     |     |     | 365 |     |     |     |     | 370 |     |     |     |     |     |
| TCC | TTT | GTC | AAC | TTT | GCT | CGT | GGT | ACC | ACT | ACT | ACT | CGT | TCC | TTT | GAC | 1444 |
| Ser | Phe | Val | Asn | Phe | Ala | Arg | Gly | Thr | Thr | Thr | Thr | Arg | Ser | Phe | Asp |     |
| 375 |     |     |     | 380 |     |     |     |     | 385 |     |     |     |     | 390 |     |     |
| TTT | GAA | ATT | GAG | ACC | AAG | CAG | GGC | ACT | CAG | TAT | ACC | TTC | AGC | AGC | ATT | 1492 |
| Phe | Glu | Ile | Glu | Thr | Lys | Gln | Gly | Thr | Gln | Tyr | Thr | Phe | Ser | Ser | Ile |     |
|     |     |     | 395 |     |     |     |     | 400 |     |     |     |     | 405 |     |     |     |
| GAG | AGG | GAG | GAG | TAC | GGG | AAA | CTG | TTT | GAT | TTT | GTC | AAC | GCG | AAA | AAG | 1540 |
| Glu | Arg | Glu | Glu | Tyr | Gly | Lys | Leu | Phe | Asp | Phe | Val | Asn | Ala | Lys | Lys |     |
|     |     | 410 |     |     |     |     | 415 |     |     |     |     | 420 |     |     |     |     |
| CTC | AAC | ATC | AAA | AAC | CGA | GGA | TTG | AAA | GAG | GGC | ATG | AAC | CCA | AGC | TAC | 1588 |
| Leu | Asn | Ile | Lys | Asn | Arg | Gly | Leu | Lys | Glu | Gly | Met | Asn | Pro | Ser | Tyr |     |
|     |     | 425 |     |     |     |     | 430 |     |     |     |     | 435 |     |     |     |     |
| GAT | GAA | TAT | GCT | GAC | TCT | GAT | GAG | GAC | CAG | CAT | GAT | GCC | TAC | TTG | GAG | 1636 |
| Asp | Glu | Tyr | Ala | Asp | Ser | Asp | Glu | Asp | Gln | His | Asp | Ala | Tyr | Leu | Glu |     |
|     | 440 |     |     |     |     | 445 |     |     |     |     | 450 |     |     |     |     |     |

```
AGG ATG AAG GAG GAA GGC AAG ATC CGG GAG GAG AAT GCC AAT GAC AGC      1684
Arg Met Lys Glu Glu Gly Lys Ile Arg Glu Glu Asn Ala Asn Asp Ser
455             460                 465                 470

AGC GAT GAC TCA GGA GAA GAA ACC GAT GAG TCA TTC AAC CCA GGT GAA      1732
Ser Asp Asp Ser Gly Glu Glu Thr Asp Glu Ser Phe Asn Pro Gly Glu
                475                 480                 485

GAG GAG GAA GAT GTG GCA GAG GAG TTT GAC AGC AAC GCC TCT GCC AGC      1780
Glu Glu Glu Asp Val Ala Glu Glu Phe Asp Ser Asn Ala Ser Ala Ser
            490                 495                 500

TCC TCC AGT AAT GAG GGT GAC AGT GAC CGG GAT GAG AAG AAG CGG AAA      1828
Ser Ser Ser Asn Glu Gly Asp Ser Asp Arg Asp Glu Lys Lys Arg Lys
        505                 510                 515

CAG CTC AAA AAG GCC AAG ATG GCC AAG GAC CGC AAG AGC CGC AAG AAG      1876
Gln Leu Lys Lys Ala Lys Met Ala Lys Asp Arg Lys Ser Arg Lys Lys
520                 525                 530

CCT GTG GAG GTG AAG AAG GGC AAA GAC CCC AAT GCC CCC AAG AGG CCC      1924
Pro Val Glu Val Lys Lys Gly Lys Asp Pro Asn Ala Pro Lys Arg Pro
535                 540                 545                 550

ATG TCT GCA TAC ATG CTG TGG CTC AAT GCC AGC CGA GAG AAG ATC AAG      1972
Met Ser Ala Tyr Met Leu Trp Leu Asn Ala Ser Arg Glu Lys Ile Lys
                555                 560                 565

TCA GAC CAT CCT GGC ATC AGC ATC ACG GAT CTT TCC AAG AAG GCA GGC      2020
Ser Asp His Pro Gly Ile Ser Ile Thr Asp Leu Ser Lys Lys Ala Gly
                570                 575                 580

GAG ATC TGG AAG GGA ATG TCC AAA GAG AAG AAA GAG GAG TGG GAT CGC      2068
Glu Ile Trp Lys Gly Met Ser Lys Glu Lys Lys Glu Glu Trp Asp Arg
            585                 590                 595

AAG GCT GAG GAT GCC AGG AGG GAC TAT GAA AAA GCC ATG AAA GAA TAT      2116
Lys Ala Glu Asp Ala Arg Arg Asp Tyr Glu Lys Ala Met Lys Glu Tyr
        600                 605                 610

GAA GGG GGC CGA GGC GAG TCT TCT AAG AGG GAC AAG TCA AAG AAG AAG      2164
Glu Gly Gly Arg Gly Glu Ser Ser Lys Arg Asp Lys Ser Lys Lys Lys
615                 620                 625                 630

AAG AAA GTA AAG GTA AAG ATG GAA AAG AAA TCC ACG CCC TCT AGG GGC      2212
Lys Lys Val Lys Val Lys Met Glu Lys Lys Ser Thr Pro Ser Arg Gly
                635                 640                 645

TCA TCA TCC AAG TCG TCC TCA AGG CAG CTA AGC GAG AGC TTC AAG AGC      2260
Ser Ser Ser Lys Ser Ser Ser Arg Gln Leu Ser Glu Ser Phe Lys Ser
                650                 655                 660

AAA GAG TTT GTG TCT AGT GAT GAG AGC TCT TCG GGA GAG AAC AAG AGC      2308
Lys Glu Phe Val Ser Ser Asp Glu Ser Ser Ser Gly Glu Asn Lys Ser
            665                 670                 675

AAA AAG AAG AGG AGG AGG AGC GAG GAC TCT GAA GAA GAA GAA CTA GCC      2356
Lys Lys Lys Arg Arg Arg Ser Glu Asp Ser Glu Glu Glu Glu Leu Ala
        680                 685                 690

AGT ACT CCC CCC AGC TCA GAG GAC TCA GCG TCA GGA TCC GAT GAG          2401
Ser Thr Pro Pro Ser Ser Glu Asp Ser Ala Ser Gly Ser Asp Glu
695                 700                 705

TAGAAACGGA GGAAGGTTCT CTTTGCGCTT GCCTTCTCAC ACCCCCCGAC TCCCCACCCA    2461

TATTTTGGTA CCAGTTTCTC CTCATGAAAT GCAGTCCCTG GATTCTGTGC CATCTGAACA    2521

TGCTCTCCTG TTGGTGTGTA TGTCACTAGG GCAGTGGGGA GACGTCTTAA CTCTGCTGCT    2581

TCCCAAGGAT GGCTGTTTAT AATTTGGGGA GAGATAGGGT GGGAGGCAGG GCAATGCAGG    2641

ATCCAAATCC TCATCTTACT TTCCCGACCT TAAGGATGTA GCTGCTGCTT GTCCTGTTCA    2701

AGTTGCTGGA GCAGGGGTCA TGTGAGGCCA GGCCTGTAGC TCCTACCTGG GGCCTATTTC    2761

TACTTTCATT TTGTATTTCT GGTCTGTGAA AATGATTTAA TAAAGGGAAC TGACTTTGGA    2821

AACCAAAAAA AGGAATTC                                                  2839
```

(2) INFORMATION FOR SEQ ID NO:2:

(i) SEQUENCE CHARACTERISTICS:
        (A) LENGTH: 709 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ala Glu Thr Leu Glu Phe Asn Asp Val Tyr Gln Glu Val Lys Gly
 1               5                  10                  15

Ser Met Asn Asp Gly Arg Leu Arg Leu Ser Arg Gln Gly Ile Ile Phe
             20                  25                  30

Lys Asn Ser Lys Thr Gly Lys Val Asp Asn Ile Gln Ala Gly Glu Leu
         35                  40                  45

Thr Glu Gly Ile Trp Arg Arg Val Ala Leu Gly His Gly Leu Lys Leu
     50                  55                  60

Leu Thr Lys Asn Gly His Val Tyr Lys Tyr Asp Gly Phe Arg Glu Ser
 65                  70                  75                  80

Glu Phe Glu Lys Leu Ser Asp Phe Phe Lys Thr His Tyr Arg Leu Glu
                 85                  90                  95

Leu Met Glu Lys Asp Leu Cys Val Lys Gly Trp Asn Trp Gly Thr Val
            100                 105                 110

Lys Phe Gly Gly Gln Leu Leu Ser Phe Asp Ile Gly Asp Gln Pro Val
        115                 120                 125

Phe Glu Ile Pro Leu Ser Asn Val Ser Gln Cys Thr Thr Gly Lys Asn
130                 135                 140

Glu Val Thr Leu Glu Phe His Gln Asn Asp Asp Ala Glu Val Ser Leu
145                 150                 155                 160

Met Glu Val Arg Phe Tyr Val Pro Pro Thr Gln Glu Asp Gly Val Asp
                165                 170                 175

Pro Val Glu Ala Phe Ala Gln Asn Val Leu Ser Lys Ala Asp Val Ile
            180                 185                 190

Gln Ala Thr Gly Asp Ala Ile Cys Ile Phe Arg Glu Leu Gln Cys Leu
        195                 200                 205

Thr Pro Arg Gly Arg Tyr Asp Ile Arg Ile Tyr Pro Thr Phe Leu His
210                 215                 220

Leu His Gly Lys Thr Phe Asp Tyr Lys Ile Pro Tyr Thr Thr Val Leu
225                 230                 235                 240

Arg Leu Phe Leu Leu Pro His Lys Asp Gln Arg Gln Met Phe Phe Val
                245                 250                 255

Ile Ser Leu Asp Pro Pro Ile Lys Gln Gly Gln Thr Arg Tyr His Phe
            260                 265                 270

Leu Ile Leu Leu Phe Ser Lys Asp Glu Asp Ile Ser Leu Thr Leu Asn
        275                 280                 285

Met Asn Glu Glu Glu Val Glu Lys Arg Phe Glu Gly Arg Leu Thr Lys
            290                 295                 300

Asn Met Ser Gly Ser Leu Tyr Glu Met Val Ser Arg Val Met Lys Ala
305                 310                 315                 320

Leu Val Asn Arg Lys Ile Thr Val Pro Gly Asn Phe Gln Gly His Ser
                325                 330                 335

Gly Ala Gln Cys Ile Thr Cys Ser Tyr Lys Ala Ser Ser Gly Leu Leu
            340                 345                 350
```

```
Tyr Pro Leu Glu Arg Gly Phe Ile Tyr Val His Lys Pro Pro Val His
        355                 360                 365

Ile Arg Phe Asp Glu Ile Ser Phe Val Asn Phe Ala Arg Gly Thr Thr
        370                 375                 380

Thr Thr Arg Ser Phe Asp Phe Glu Ile Glu Thr Lys Gln Gly Thr Gln
385                 390                 395                 400

Tyr Thr Phe Ser Ser Ile Glu Arg Glu Glu Tyr Gly Lys Leu Phe Asp
                405                 410                 415

Phe Val Asn Ala Lys Lys Leu Asn Ile Lys Asn Arg Gly Leu Lys Glu
                420                 425                 430

Gly Met Asn Pro Ser Tyr Asp Glu Tyr Ala Asp Ser Asp Glu Asp Gln
                435                 440                 445

His Asp Ala Tyr Leu Glu Arg Met Lys Glu Gly Lys Ile Arg Glu
    450                 455                 460

Glu Asn Ala Asn Asp Ser Ser Asp Asp Ser Gly Glu Glu Thr Asp Glu
465                 470                 475                 480

Ser Phe Asn Pro Gly Glu Glu Glu Asp Val Ala Glu Glu Phe Asp
                485                 490                 495

Ser Asn Ala Ser Ala Ser Ser Ser Asn Glu Gly Asp Ser Asp Arg
                500                 505                 510

Asp Glu Lys Lys Arg Lys Gln Leu Lys Lys Ala Lys Met Ala Lys Asp
        515                 520                 525

Arg Lys Ser Arg Lys Lys Pro Val Glu Val Lys Lys Gly Lys Asp Pro
        530                 535                 540

Asn Ala Pro Lys Arg Pro Met Ser Ala Tyr Met Leu Trp Leu Asn Ala
545                 550                 555                 560

Ser Arg Glu Lys Ile Lys Ser Asp His Pro Gly Ile Ser Ile Thr Asp
                565                 570                 575

Leu Ser Lys Lys Ala Gly Glu Ile Trp Lys Gly Met Ser Lys Glu Lys
        580                 585                 590

Lys Glu Glu Trp Asp Arg Lys Ala Glu Asp Ala Arg Arg Asp Tyr Glu
        595                 600                 605

Lys Ala Met Lys Glu Tyr Glu Gly Gly Arg Gly Glu Ser Ser Lys Arg
        610                 615                 620

Asp Lys Ser Lys Lys Lys Lys Val Lys Val Lys Met Glu Lys Lys
625                 630                 635                 640

Ser Thr Pro Ser Arg Gly Ser Ser Ser Lys Ser Ser Ser Arg Gln Leu
                645                 650                 655

Ser Glu Ser Phe Lys Ser Lys Glu Phe Val Ser Ser Asp Glu Ser Ser
                660                 665                 670

Ser Gly Glu Asn Lys Ser Lys Lys Lys Arg Arg Arg Ser Glu Asp Ser
        675                 680                 685

Glu Glu Glu Glu Leu Ala Ser Thr Pro Pro Ser Ser Glu Asp Ser Ala
    690                 695                 700

Ser Gly Ser Asp Glu
705

(2) INFORMATION FOR SEQ ID NO:3:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:3:
```

```
CCTCTCTGGT TCTTC                                                          15
```

(2) INFORMATION FOR SEQ ID NO:4:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:4:

```
Met Lys Lys Lys Phe
1               5
```

(2) INFORMATION FOR SEQ ID NO:5:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:5:

```
Met Lys Lys Lys Phe Asp Pro Asn Ala Pro Lys
1               5                   10
```

(2) INFORMATION FOR SEQ ID NO:6:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:6:

```
Met Lys Lys Lys Phe Lys Asp Pro Asn
1               5
```

(2) INFORMATION FOR SEQ ID NO:7:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:7:

```
Met Lys Lys Lys Phe Lys
1               5
```

(2) INFORMATION FOR SEQ ID NO:8:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:8:

```
Met Lys Lys Lys Phe Lys Asp Pro Asn Ala Pro Lys Arg
1               5                   10
```